United States Patent
Cao et al.

(10) Patent No.: US 10,289,283 B1
(45) Date of Patent: May 14, 2019

(54) VISUAL ANALYSIS FOR MULTI-DIMENSIONAL DATA

(71) Applicant: EMC Corporation, Hopkinton, MA (US)

(72) Inventors: Yu Cao, Beijing (CN); Baoyao Zhou, Beijing (CN); Ricky Sun, Beijing (CN); Demetrios Fanourgiakis, Toronto (CA); Min Zhu, Sichuan (CN); Mingzhao Li, Chengdu (CN); Ting Liang, Sichuan (CN); Qihong Gan, Sichuan (CN); Yabo Su, Sichuan (CN)

(73) Assignee: EMC IP Holding Company LLC, Hopkinton, MA (US)

( * ) Notice: Subject to any disclaimer, the term of this patent is extended or adjusted under 35 U.S.C. 154(b) by 468 days.

(21) Appl. No.: 14/500,247

(22) Filed: Sep. 29, 2014

(51) Int. Cl.
| | |
|---|---|
| *G06F 19/26* | (2011.01) |
| *G06F 3/0484* | (2013.01) |
| *G06T 11/20* | (2006.01) |
| *G06F 17/17* | (2006.01) |
| *G06F 12/02* | (2006.01) |

(52) U.S. Cl.
CPC .......... *G06F 3/04842* (2013.01); *G06F 19/26* (2013.01); *G06T 11/206* (2013.01); *G06F 12/0207* (2013.01); *G06F 17/175* (2013.01); *G06T 2200/24* (2013.01)

(58) Field of Classification Search
CPC .... G06F 19/26; G06F 17/175; G06F 12/0207; G06F 19/24
See application file for complete search history.

(56) References Cited

U.S. PATENT DOCUMENTS

| | | | |
|---|---|---|---|
| 9,043,266 B2 * | 5/2015 | Bauerle | G06F 17/30017 707/601 |
| 2006/0101324 A1 * | 5/2006 | Goldberg | G06F 17/245 715/227 |

(Continued)

OTHER PUBLICATIONS

Hayashi et al. (Sep. 15, 2014, The Journal of the Society for Art and Science, vol. 13, No. 3, Index p. 1-4, pp. 185-197).*

(Continued)

*Primary Examiner* — Shen Shiau
(74) *Attorney, Agent, or Firm* — Ryan, Mason & Lewis, LLP

(57) ABSTRACT

A set of multidimensional data is obtained. At least a portion of the set of multidimensional data is processed to generate a set of formatted data, wherein the set of formatted data comprises at least one of attributes, attribute values and statistics on attribute values. A user is enabled to select, on a graphical user interface, an analysis task to be performed on at least a portion of the set of formatted data. One or more visualizations are generated from a set of visualization types for presentation on a graphical user interface to the user. The set of visualization types comprises a first visualization type representing a relationship between two attributes whereby attribute value pairs are represented by varying colors, a second visualization type representing thematic variations over time with respect to values of at least one attribute; and a third visualization type representing values of three attributes comprising one or more histograms. The one or more generated visualizations are based on the selected analysis task.

20 Claims, 15 Drawing Sheets

(56) References Cited

U.S. PATENT DOCUMENTS

| | | | | |
|---|---|---|---|---|
| 2009/0033664 | A1* | 2/2009 | Hao | G06T 11/206 |
| | | | | 345/440 |
| 2010/0318934 | A1* | 12/2010 | Blevins | G05B 13/048 |
| | | | | 715/772 |
| 2013/0307843 | A1* | 11/2013 | Sikka | G06T 15/00 |
| | | | | 345/419 |
| 2016/0034164 | A1* | 2/2016 | High | G06F 3/04847 |
| | | | | 715/773 |
| 2016/0055221 | A1* | 2/2016 | Paquette | G06F 17/30601 |
| | | | | 707/722 |
| 2016/0092530 | A1* | 3/2016 | Jakubiak | G06F 17/30572 |
| | | | | 715/202 |

OTHER PUBLICATIONS

Havre, B. Hetzler, L. Nowell, ThemeRiver: Visualizing Theme Changes over Time, IEEE Symp. on Information Visualization, 115 123, 2000.*

A. Kobayashi et al., "Edge Equalized Treemaps," Proceedings of the 16th International Conference on Information Visualisation (IV), Jul. 2012, pp. 7-12, Montpellier, France.

S. Havre et al, "ThemeRiver: Visualizing Thematic Changes in Large Document Collections," IEEE Transactions on Visualization and Computer Graphics, Jan./Mar. 2002, pp. 9-20, vol. 8, No. 1.

J. Xia et al., "An Online Visualization System for Streaming Log Data of Computing Cluster," Tsinghua Science and Technology, Apr. 2013, pp. 196-205, vol. 18, No. 2.

A. Pryke et al., "Heatmap Visualisation of Population Based Multi Objective Algorithms," Proceedings of the 4th International Conference on Evolutionary Multi-Criterion Optimization (EMO), Lecture Notes in Computer Science, Mar. 2007, pp. 361-375, Matsushima, Japan, vol. 4403.

* cited by examiner

VISUAL ANALYSIS FOR MULTI-DIMENSIONAL DATA

FIELD

The field relates to data processing, and more particularly to visual analysis methodologies for multi-dimensional data.

BACKGROUND

With the rapid development of information technology (IT), the generation of multi-dimensional information is increasing in fields such as, by way of example, science, engineering and business. For example, with the popularization of mobile devices, a mass of log data is typically collected when users visit mobile websites (i.e., the mobile Internet). The data includes dimensions or attributes such as, for example, date and time of visit, visited website name, device brand used to visit the website, device operating system and Internet browser used to visit the website. This multi-dimensional data represents the various Internet browsing behaviors associated with users. How to more effectively understand and analyze the rich content of this multi-dimensional data has become an important issue to be addressed.

SUMMARY

Embodiments of the present invention provide visual analysis methodologies for multi-dimensional data.

For example, in one embodiment, a method comprises the following steps. A set of multidimensional data is obtained. At least a portion of the set of multidimensional data is processed to generate a set of formatted data, wherein the set of formatted data comprises at least one of attributes, attribute values and statistics on attribute values. A user is enabled to select, on a graphical user interface, an analysis task to be performed on at least a portion of the set of formatted data. One or more visualizations are generated from a set of visualization types for presentation on a graphical user interface to the user. The set of visualization types comprises a first visualization type representing a relationship between two attributes whereby attribute value pairs are represented by varying colors, a second visualization type representing thematic variations over time with respect to values of at least one attribute; and a third visualization type representing values of three attributes comprising one or more histograms. The one or more generated visualizations are based on the selected analysis task.

In another embodiment, an article of manufacture is provided which comprises a processor-readable storage medium having encoded therein executable code of one or more software programs. The one or more software programs when executed by at least one processing device implement steps of the above-described method.

In a further embodiment, an apparatus comprises a memory and a processor operatively coupled to the memory and configured to perform steps of the above-described method.

Advantageously, illustrative embodiments provide visual analysis methodologies for multi-dimensional log data, which combine three visualization techniques (e.g., heat map, theme river and histomatrix) to transform the multi-dimensional log data into interactive views, so as to enable users to analyze the correlation between a single attribute and time, the correlation between two attributes, or the correlation among three attributes of the log data.

These and other features and advantages of the present invention will become more readily apparent from the accompanying drawings and the following detailed description.

DETAILED DESCRIPTION

Illustrative embodiments of the present invention will be described herein with reference to exemplary data processing systems, computing systems, data storage systems and associated servers, computers, storage units and devices and other processing devices. It is to be appreciated, however, that embodiments of the invention are not restricted to use with the particular illustrative system and device configurations shown. Moreover, the phrases "data processing system," "computing system" and "data storage system" as used herein are intended to be broadly construed, so as to encompass, for example, private or public cloud computing or storage systems, as well as other types of systems comprising distributed virtual infrastructure. However, a given embodiment may more generally comprise any arrangement of one or more processing devices.

Illustrative embodiments implement visualization generation and analysis techniques coupled with human intelligence through a visual perception channel (visual analytics). Such techniques, enable problems to be addressed, whose size and complexity make them otherwise intractable. The tasks performed in accordance with these techniques such as, but not limited to, understanding data, reasoning and making decisions, can be completed interactively. Completion of the tasks mainly involves data representation, data transformation, visual representation, interaction and analytical reasoning techniques, as will be further explained herein.

Before describing illustrative embodiments of the invention, we first describe some illustrative visualization software tools that can be employed in illustrative embodiments.

Figure 1:
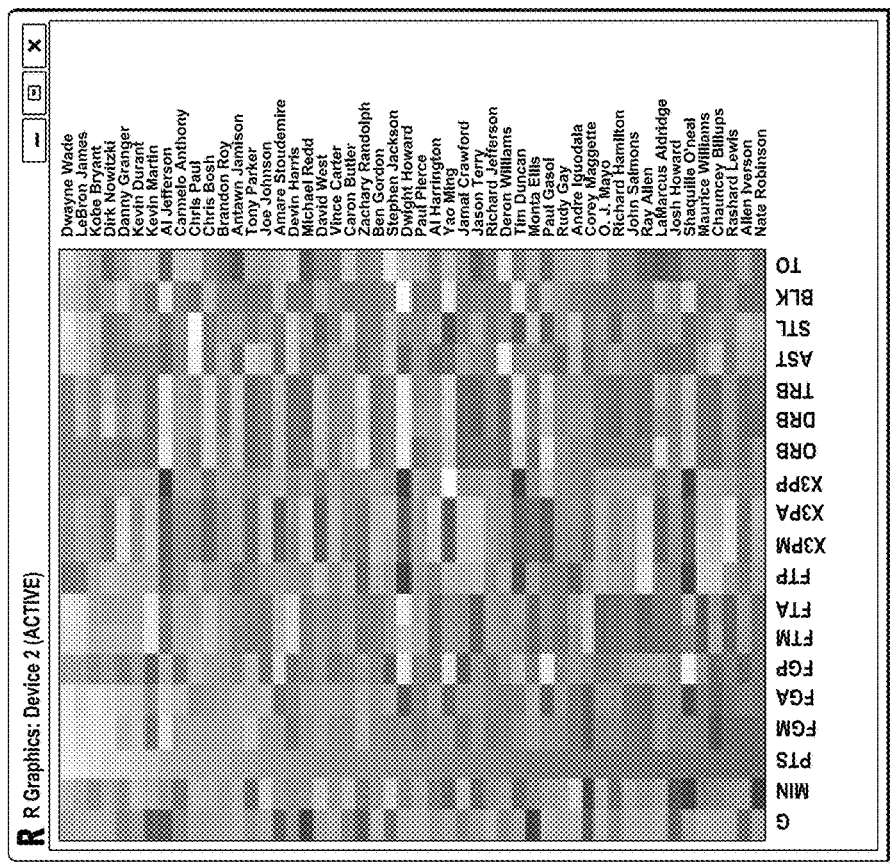
FIG. 1 shows an example of a heat map type of visualization in accordance with which one or more embodiments of the invention are implemented.

A heat map is a graphical representation (visualization) of data where the individual values contained in a matrix are represented as colors. A heat map originated as two-dimensional (2D) displays of the values in a data matrix. Larger values were represented by small dark gray or black squares (pixels) and smaller values by lighter squares. A heat map is applicable to visualizing the relationship between two attributes (dimensions). The horizontal and vertical axes respectively represent Attribute I and Attribute II. In contrast to conventional line charts and scatter plots, a heat map reduces crossing of lines and overlapping of the points, and thereby reduces the visual confusion to make the observation clearer. This method is suitable for analyzing the single attribute distribution along with time, or the correlation between two attributes. FIG. 1 shows a heat map generated from the National Basketball Association (NBA) statistical data of 2008. The horizontal axis (Attribute I) shows various statistical indexes of the NBA such as PTS (Points), and the vertical axis (Attribute II) shows the names of various NBA players. Each value pair of Attribute I and Attribute II, representing the score on a specific item, is typically mapped to a colored rectangle, where white color typically corresponds to a maximum (max) value and red typically corresponds to a minimum (min) value. However, in the current gray scale version of the map visualization 100 shown in FIG. 1, white corresponds to a max value and black corresponds to a min value (with various gray scale shading in between). Note that due to USPTO limitations on the use of certain color figures, the visualizations presented herein will be in gray scale (rather than colors). However, where needed, an explanation will be given as to how certain colors in the actual visualizations displayed to the users will appear. An example of a heat map rendering algorithm is described in A. Pryke et al., "Heatmap Visualization of Population Based Multi Objective Algorithms," Evolutionary Multi-Criterion Optimization, LNCS 4403, pp. 361-375, Springer, 2007. Note that one example of a heat map view is a "HeatMap view" generated with the HeatMap technique in this article.

Figure 2:
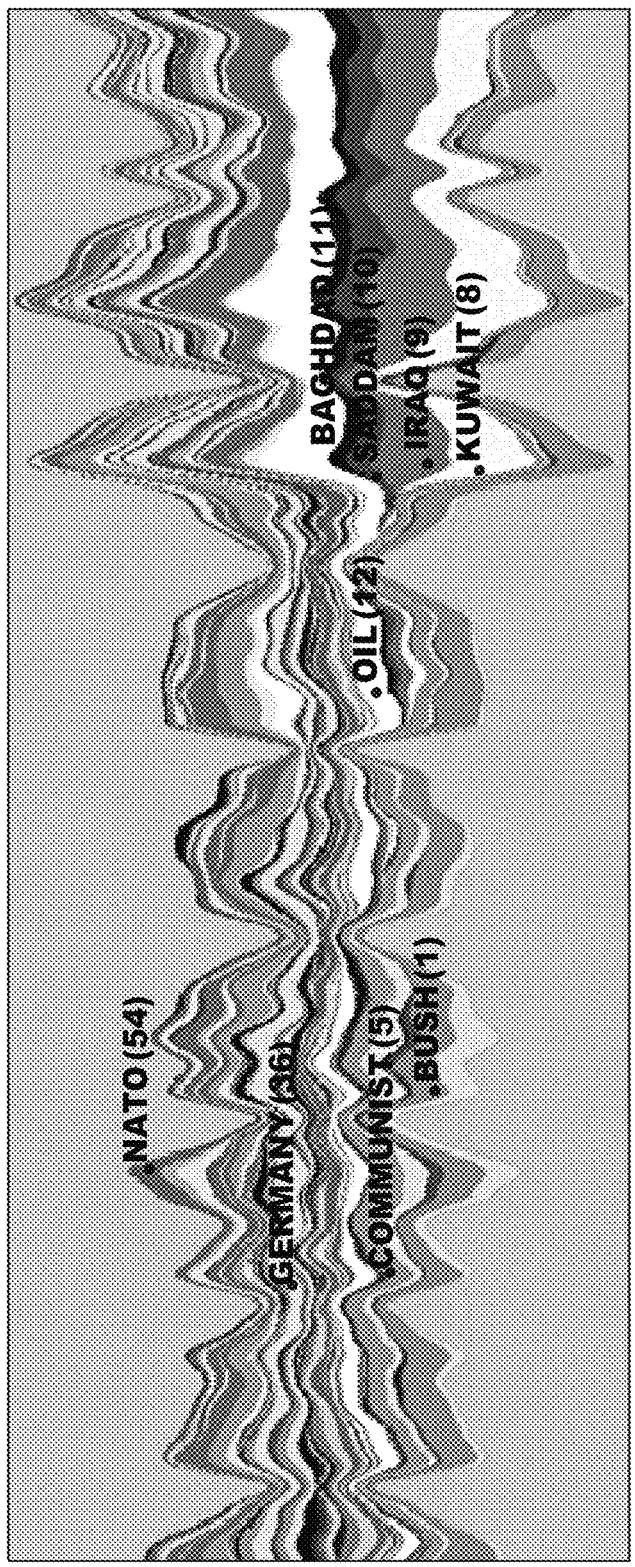
FIG. 2 shows an example of a theme river type of visualization in accordance with which one or more embodiments of the invention are implemented.

A theme river visualizes thematic variations over time within a large collection of documents. The "river" flows from left to right through time, changing width to depict changes in thematic strength of temporally associated documents. Typically, colored "currents" flowing within the river narrow or widen to indicate decreases or increases in the strength of an individual topic or a group topic in the associated documents. The river is shown within the context of a timeline and a corresponding textual presentation of external events. The method is also applicable to temporal data, and a user can analyze the changing trends over time of the specific attribute within the data. FIG. 2 shows a theme river 200 generated using Associated Press data from July-August 1990. A wide current in the river indicates heavy use of a topic, while changes in color (gray scale in the version shown in FIG. 2) distribution correlate to changes in themes. An example of a theme river rendering algorithm is described in S. Havre et al., "ThemeRiver: Visualizing Thematic Changes in Large Document Collections," IEEE Transactions on Visualization and Computer Graphics, vol. 8, no. 1, pp. 9-20, 2002. Note that one example of a theme river view is a "ThemeRiver view" generated with the ThemeRiver technique in this article.

Figure 3:
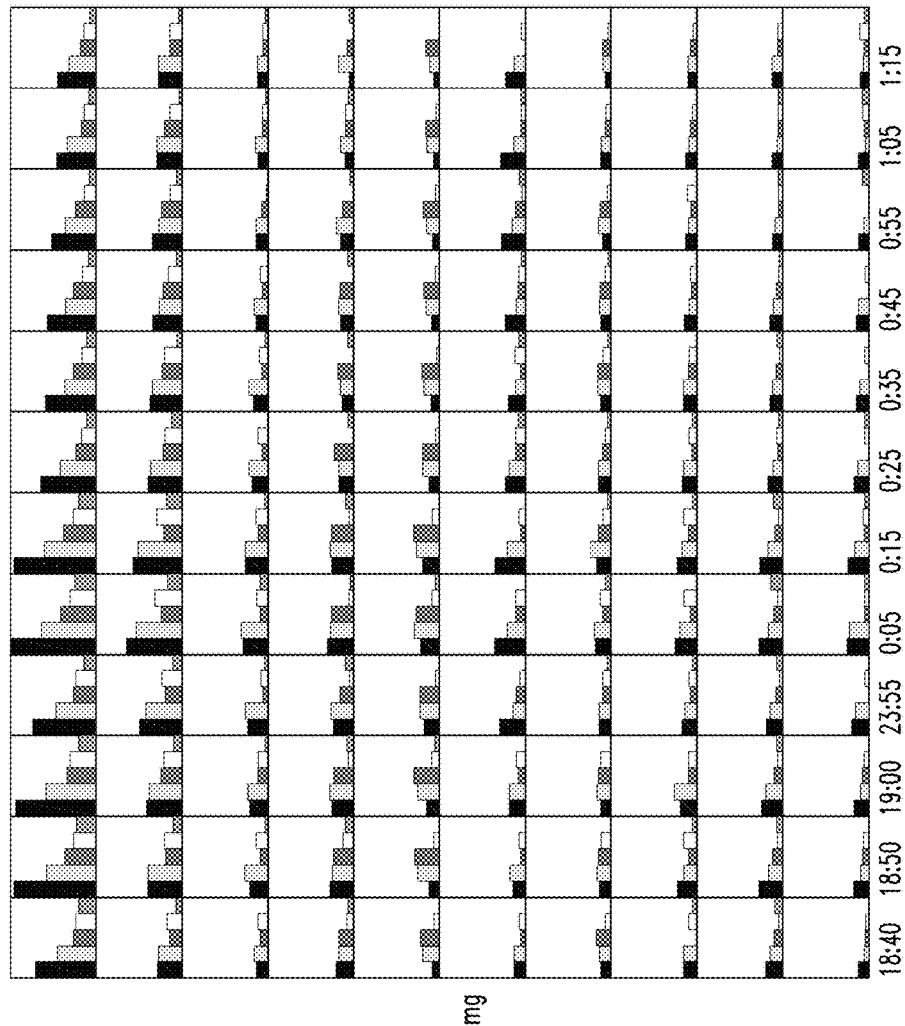
FIG. 3 shows an example of a histomatrix type of visualization in accordance with which one or more embodiments of the invention are implemented.

A histomatrix adapts a grid representation with embedded histograms to visualize three-dimensional data. For example, Time (Attribute I) and a main attribute (Attribute II) are respectively mapped as horizontal and vertical axes, and then the view is divided into several orthogonal grids with the subdivision of Attribute I and II. The histogram is drawn in each grid to show another attribute (Attribute III), and different colors of the bar in the histogram typically represent the different values of Attribute III. Compared with other high-dimensional data visualization methods, such as parallel coordinates, this method has lower requirements for the continuity of the data attributes, and it also avoids visual clutter generated by the overlapping of lines. It is realized herein that it is better to adapt a histomatrix to analyze the relationships among three attributes considering the characteristic of high dispersion in log data attributes distribution. In the histomatrix view 300 shown in FIG. 3, the horizontal axis represents time (Attribute I) and the vertical axis represents websites (Attribute II). Histograms embedded in each grid correspond to various mobile operating systems (Attribute III). Different gray scale shadings in FIG. 3 correspond to different operating systems and the height of the histogram bars reveals the number of devices running a specific operating system in a specific time period. Thus, a histomatrix realizes the visualization of three attributes. An example of a histomatrix rendering algorithm is described in A. Kobayashi et al., "Edge Equalized Treemaps," 16th International Conference on Information Visualization (IV), pp. 7-12, 2012. Note that one example of a histomatrix view is a "HistoMatrix view" generated with the HistoMatrix technique in this article.

Illustrative embodiments provide visual analysis methodologies for multi-dimensional log data, which combine the three visualization techniques (heat map, theme river and histomatrix) to transform the multi-dimensional log data into interactive views, so as to enable users to analyze the correlation between a single attribute and time, the correlation between two attributes, or the correlation among three attributes of the log data.

Moreover, illustrative embodiments provide methodologies for the analysis of time-related cross attributes, which includes analyzing the variation of a specific attribute I over time, and analyzing data characteristics of three attributes (Attribute I×Attribute II×Time), where attribute H is associated with attribute I (i.e., Attribute I and II are called cross attributes). Illustrative embodiments integrate the three visualization techniques (heat map, theme river and histomatrix) in a progressively interactive manner. Firstly, illustrative embodiments enable users to analyze the general characteristics of Attribute I×Time with a heat map view. Then, illustrative embodiments enable users to interactively select the elements of Attribute I to generate a theme river view for further analysis on focused elements. Also, according to the selections of the elements in the heat map and Attribute II, illustrative embodiments enable users to generate a histomatrix view to analyze the three-dimensional data on Attribute I×Attribute II×Time. Finally, repeating of the above processes, illustrative embodiments enable users to realize the progressive and interactive analysis of time-related cross attributes.

It is to be appreciated that reference below to a user selecting, zooming, viewing, analyzing and/or similar actions, can be accomplished through conventional display devices (e.g., computer screen, smartphone screen, etc.) and conventional pointing devices (e.g., mouse, trackpad, touchscreen, etc.) interacting in a conventional manner known to those of ordinary skill in the art in conjunction with one or more graphical user interfaces implemented via one or more computing devices or systems.

Figure 4:
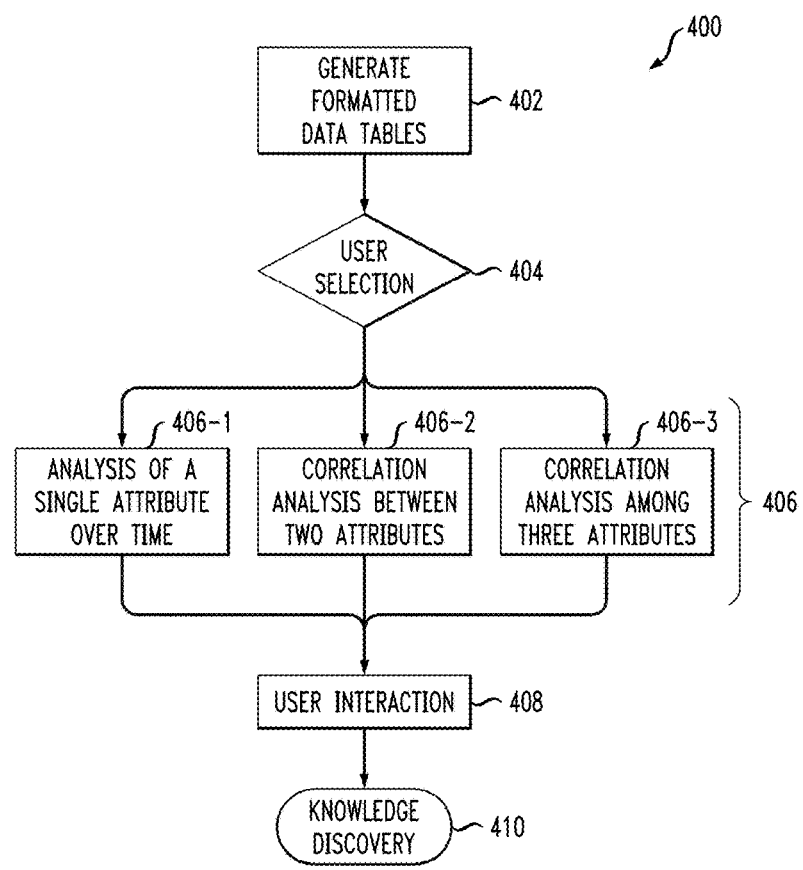
FIG. 4 shows a visualization methodology for analysis of multi-dimensional log data in accordance with one embodiment of the invention.

Accordingly, by way of example, FIG. 4 shows an illustrative embodiment of a visualization methodology 400 for analysis of multi-dimensional log data. The methodology involves three concepts: attribute, attribute value and statistics on attribute value. Attributes represent the meaningful information contained by the log data, such as, for example, date and time, visited website name, device brand, device operating system and Internet browser. An attribute may have one or multiple possible attribute values. For instance, an attribute "website" may have values such as "Google," "Facebook," "Amazon," etc. In the log data, a specific attribute value may be associated with some (temporal) statistics information, e.g., a website value "Google" was visited 1000 times during a specific time period. As shown in FIG. 4, methodology 400 proceeds as follows:

Step 402: Generate formatted tables from the log data. Assume there are n attributes ($A_1, \ldots, A_i, \ldots, A_n$), including time attribute T. Conventional data mining techniques can be utilized to parse the log data to derive two types of data tables:

Two-dimensional table Btable($A_i, A_j$): $A_i$ and $A_j$ represent two different attributes. When $A_i \neq T$ and $A_j \neq T$ BTable ($A_1, A_j$) records statistics on $A_i$ values over the time; when $A_i \neq T$ and $A_j \neq T$, BTable($A_i, A_j$) records the statistics on the correlation between $A_i$ values and $A_j$ values. Table 1 below depicts a sample BTable(Brand, T), where the entry value "24205" means the number of users surfing the Internet with a "Nokia" phone at time: 2012/4/9 18:35:00.

TABLE 1

BTable (Brand, T)

| Time | Brand | | |
|------|-------|---|---|
| | Nokia | ... | htc |
| 2012/4/9 18:35:00 | 24205 | ... | 3372 |
| ... | ... | ... | ... |
| 2012/4/10 23:55:00 | 40325 | ... | 5908 |

Three-dimensional table TTable($A_i, A_j, A_k$): this table records the statistics on the correlation among values of attributes $A_i, A_j$ and $A_k$ ($A_i \neq A_j \neq A_k$). Table 2 below depicts a sample TTable(Brand, OS, T), where the entry value "107" means the number of users surfing the Internet with a "Nokia" phone running the "Windows Phone 7" operating system (OS) at 2012/4/9 18:35:00.

TABLE 2

TTable(Brand, OS, T)

| Time | Brand + OS | | |
|------|------------|---|---|
| | Nokia + WP7 | ... | htc + android |
| 2012/4/9 18:35:00 | 107 | ... | 294 |
| ... | ... | ... | ... |
| 2012/4/11 0:30:00 | 140 | ... | 156 |

Step 404: According to the analysis objectives, a user can select from three visual analysis tasks:

1) Analysis of a single attribute's values over time, including attribute value distribution and attribute value varying trend over time (step 406-1).

2) Correlation analysis between two attributes (step 406-2), e.g., between OS and Browser.

3) Correlation analysis among three attributes (step 406-3), e.g., among Brand, OS and Time.

Step 406: According to the user's selection, interactively accomplish the corresponding visual analysis task. The details of this step will be described in detail below.

Step 408: the user may interact with the system to update the visualized views if so desired. The interaction may, by way of example, include: 1) selection of colors, attributes, and timeline scale in a theme river; and 2) selection of displayed relationships and focused records, and mouse hovering above the regions to display the specific value in a heat map. Furthermore, multiple relationships can also be displayed in a histomatrix. When the user selects the attributes in the heat map view, the histomatrix view is automatically updated with the corresponding records.

Step 410: Knowledge discovery. The user can observe the interactive visualized views to discover the changing of an attribute's values over time, to explore the correlation between two attributes or among three attributes. Taking website analysis as an example, the user can select the relation of Time&Host in the heat map, and select Host in the theme river, then the histomatrix displays the view of the corresponding relationship. Interacting with the visualized views, the user can find that, at late night, when hits of most hosts decrease, hits of a weather forecast client (which only exists in some specific operating system) increase periodically to automatically update information. Furthermore, by only selecting the host's tag on the heat map, the user can observe the trend over time of the weather host more clearly in the theme river and histomatrix views.

In the following description, we describe details of the three types of visual analysis tasks in step 406.

Figure 5:
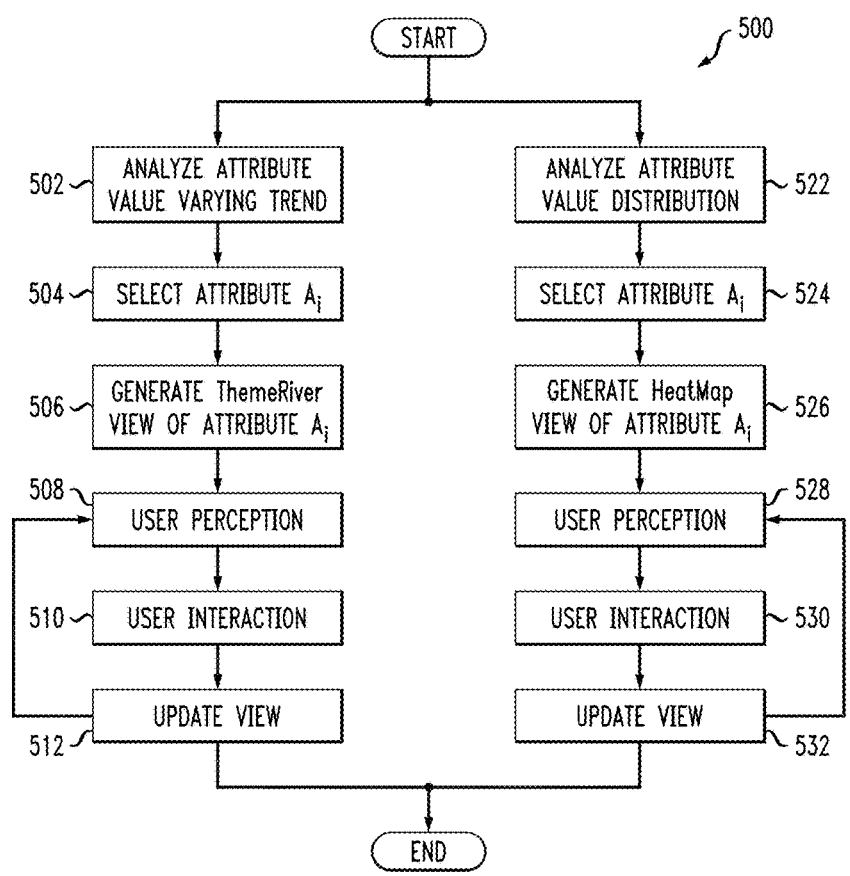
FIG. 5 shows a methodology for analyses of values of a single attribute over time including attribute value distribution and attribute value varying trend over time in accordance with one embodiment of the invention.

FIG. 5 illustrates a methodology 500 for analysis of a single attribute over time (406-1).

In an initial step, the user selects a subtask. Steps 502 through 512 assume the user selected the subtask of analyzing an attribute value varying trend, while steps 522 through 532 assume the user selected the subtask of analyzing an attribute value distribution over time.

Step 502: The user selects the subtask of analyzing an attribute value varying trend.

Step 504: The user chooses Attribute $A_i$ to be observed. According to the user's selection, a two-dimensional table BTable($A_i$, T) corresponding to attribute $A_i$ and time attribute T is generated and imported.

Step 506: the system generates an interactive theme river view of attribute $A_i$, according to BTable($A_i$, T) by applying a theme river rendering algorithm (e.g., S. Havre et al. article referenced above).

Step 508: User perception. The user observes visual features in the view generated in step 506, and analyzes the varying of statistics on $A_i$ value $a_{ij}$ over time. The user can also compare two arbitrary $A_i$ values $a_{ij}$ and $a_{jk}$ in terms of statistics and varying trends.

Step 510: User interaction. Based on the previous observations, the user can choose from interaction operations, such as, for example, adjusting the theme river ribbon's color scheme to highlight $A_i$ value $a_{ij}$ and $a_{ik}$, dragging the bidirectional slide bar of time to observe value $a_{ij}$'s statistics varying trend during a specific period of time, and changing the input attribute $A_i$ to restart the analysis.

Step 512: Update theme river view. According to the user's interaction operations, the system generates a new/updated theme river view.

Steps 508 through 512 are repeated, until the expected analysis tasks are completed.

Step 522: The user selects the subtask of analyzing an attribute value distribution.

Step 524: the user chooses Attribute $A_i$ to be observed. According to the user's selection, a two-dimensional table BTable($A_i$, T) corresponding to attribute $A_i$ and time attribute T is generated and imported.

Step 526: the system generates an interactive heat map view of attribute $A_i$, according to BTable($A_i$, T) and by applying a matrix partitioning technique whereby the display area is partitioned into multiple sub-areas.

Step 528: User perception. The user observes visual features in the view generated in step 526, and analyzes the statistics distribution of each $A_i$ value $a_{ij}$ over time.

Step 530: User interaction. According to the previous observation, the user can choose from interaction operations, such as, for example, hovering the mouse pointer above a grid to display a specific value of its data, choosing to only display and observe the statistics distribution of a subset of $A_i$ attribute values, and changing the input attribute $A_i$ to restart the analysis.

Step 532: Update the heat map view. According to the user's interaction operations, the system generates a new/updated heat map view.

Steps 528 through 532 are repeated, until the expected analysis tasks are completed.

Figure 6:
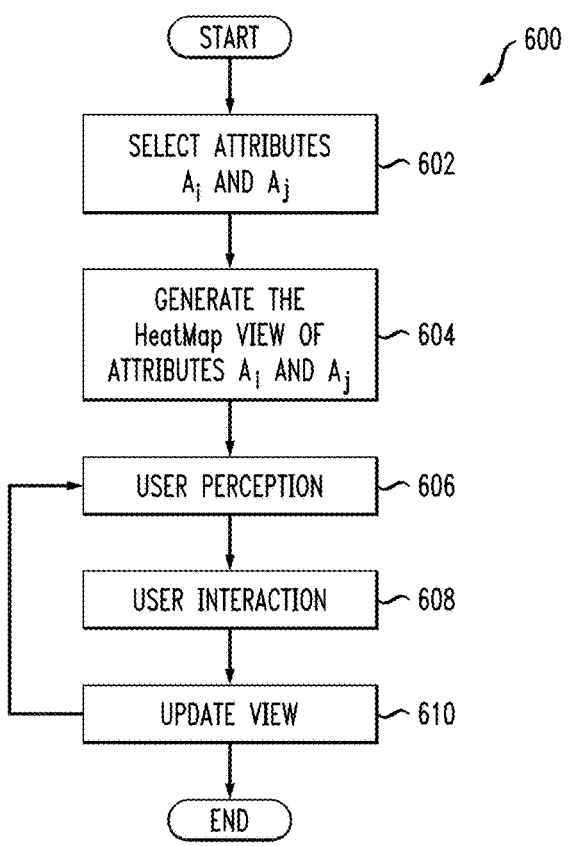
FIG. 6 shows a methodology for correlation analysis between two attributes in accordance with one embodiment of the invention.

FIG. 6 illustrates a methodology 600 for analysis between two attributes (406-2).

Step 602: The user selects attributes $A_i$ and $A_j$ ($A_i \neq T$, $A_j \neq T$) to be observed. According to the user's selection, a two-dimensional table BTable($A_i$, $A_j$) corresponding to attributes $A_i$ and $A_j$ is generated and imported.

Step 604: the system generates an interactive heat map view of attributes $A_i$ and $A_j$, according to BTable($A_i$, $A_j$) by applying the above-mentioned matrix partitioning technique.

Step 606: User perception. The user observes visual features in the view generated in step 604, and analyzes the correlation of $A_i$ and $A_j$ values.

Step 608: User interaction. According to the previous observations, the user can choose interaction operations, such as, for example, hovering the mouse pointer above a grid to display a specific value of its data, choosing to only display and observe the statistics distribution of a subset of $A_i$ (and/or $A_j$) attribute values, and changing the input attributes $A_i$ and $A_j$ to restart the analysis.

Step 610: Update the heat map view. According to the user's interaction operations, the system generates a new/updated heat map view.

Steps 606 through 610 are repeated, until the expected analysis tasks are completed.

Figure 7:
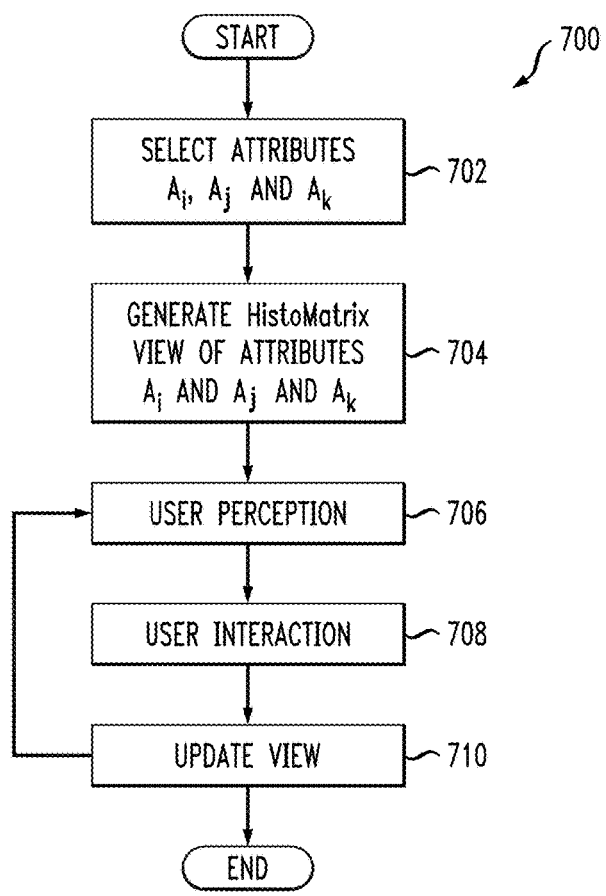
FIG. 7 shows a methodology for correlation analysis among three attributes in accordance with one embodiment of the invention.

FIG. 7 illustrates a methodology 700 for analysis among three attributes (406-3).

Step 702: The user selects attributes $A_i$, $A_j$ and $A_k$ ($A_i \neq A_j \neq A_k$) to be observed. According to the user's selections, a three-dimensional table TTable ($A_i$, $A_j$, $A_k$) is generated and imported.

Step 704: The system generates an interactive histomatrix view for attributes $A_i$, $A_j$ and $A_k$, according to TTable ($A_i$, $A_j$, $A_k$) by applying an edge equalized treemaps rendering algorithm (e.g., A. Kobayashi et al. article referenced above).

Step 706: User perception. The user observes the visual characteristics of the view generated by step 704, and analyzes the correlation of $A_i$, $A_j$ and $A_k$ values.

Step 708: User interaction. The user can apply interaction operations to find patterns, such as, for example, zooming into a specific value range of $A_i$ and focusing on the correlation of $A_i$ values in this range with $A_j$ and $A_k$ values.

Step 710: Update view. According to the user's interaction operations, the system generates a new/updated histomatrix view.

Steps 706 through 710 are repeated, until the expected analysis tasks are completed.

Illustrative embodiments also provide visualization methodologies for analysis of time-related cross attributes. It is assumed in these illustrative embodiments that the data includes three attributes (i.e., Attribute I, Attribute II and Time). We call the possible values of Attribute I (respectively, Attribute II) as the elements of Attribute I (respectively, Attribute II). The statistics of Attribute I values over time are stored in a two-dimensional table BTable(Attribute I, Time), and the statistics of the correlation among Attribute I, Attribute II and Time are stored in a three-dimensional table TTable (Attribute I, Attribute II, Time). Examples of such tables are shown above as table 1 and table 2, respectively.

Figure 8:
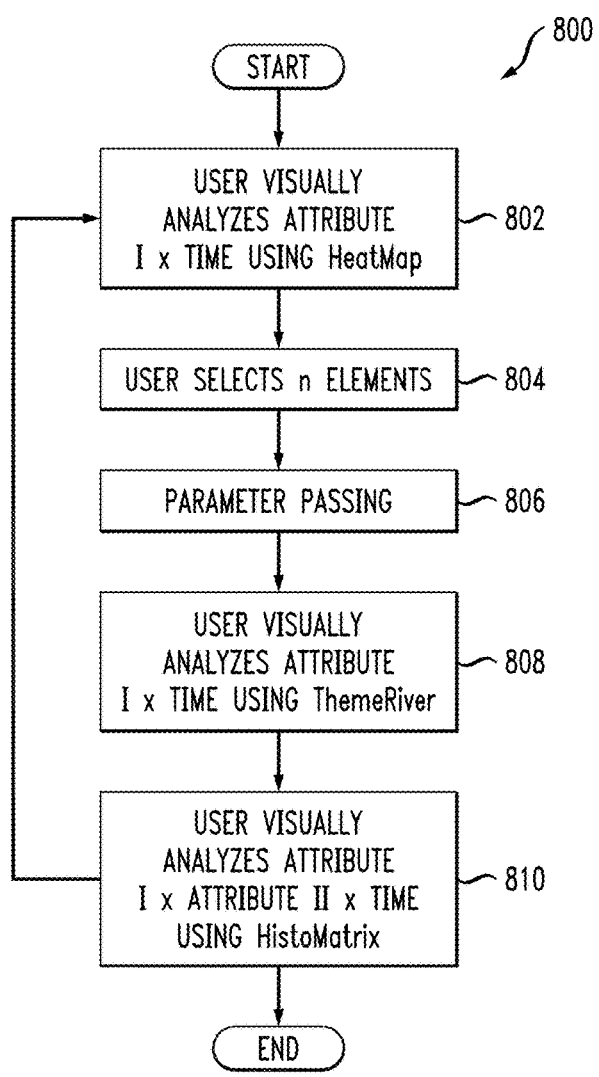
FIG. 8 shows a methodology for analysis of time-related cross attributes in accordance with one embodiment of the invention.

FIG. 8 illustrates a time-related cross attribute analysis methodology 800 according to an illustrative embodiment. The methodology proceeds as follows:

Step 802: Visual analysis using a heat map. The user analyzes the heat map view on Attribute I×Time and observes how the elements of Attribute I change over time.

Step 804: Element selection. In the heat map view, the user selects n elements, either with varying trends significantly different from the overall trend or those being of interest to user, for further analysis.

Step 806: Parameter passing. The system sets the n elements selected by the user as parameters to generate the theme river and histomatrix views.

Step 808: Visual analysis using theme river view. According to the theme river view generated based on the selected n elements of Attribute I in the heat map view, the user can focus on the variation over time of the n elements. The user can also analyze the characteristics in each period by scaling the timeline.

Step 810: Visual analysis using histomatrix view. According to the selections of the n elements in the heat map and Attribute II, the system generates a histomatrix view of Attribute I×Attribute II×Time, with which the user can focus on the data features and relationships among the three dimensions.

Steps 802 through 810 are repeated until the expected analysis tasks are completed. After visual analysis with the theme river and the histomatrix, the user can continue the analysis by returning to the heat map thus realizing an iterative, progressive and interactive analysis of time-related cross attributes.

For process of user analysis at steps 802, 808 and 810, respective detailed descriptions are presented below in the context of FIGS. 9, 10 and 11.

Figure 9:
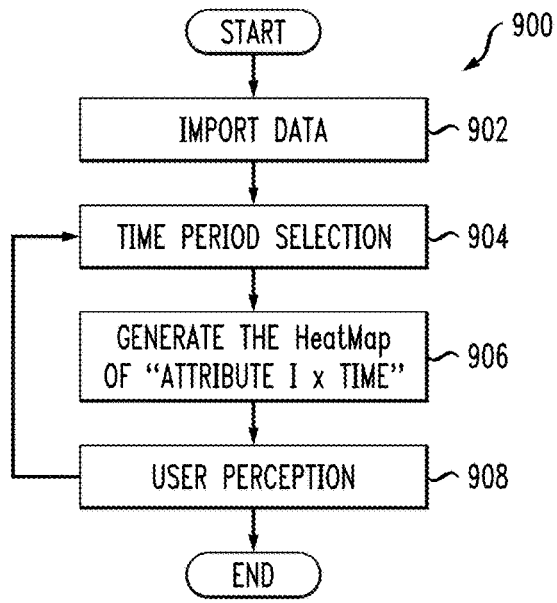
FIG. 9 shows a methodology for visual analysis using a heat map visualization in accordance with one embodiment of the invention.

FIG. 9 shows an illustrative embodiment of visual analysis methodology 900 using a heat map (step 802).

Step 902: The system imports the two-dimensional table BTable (Attribute I, Time).

Step 904: The user selects time period.

Step 906: The system reads the data of the selected time period from the BTable, and generates a heat map view of "Attribute I×Time."

Step 908: User perception. The user analyzes the heat map view and observes the trend of how each element of Attribute I changes over time.

Steps 902 through 908 are repeated until the expected analysis tasks are completed.

Figure 10:
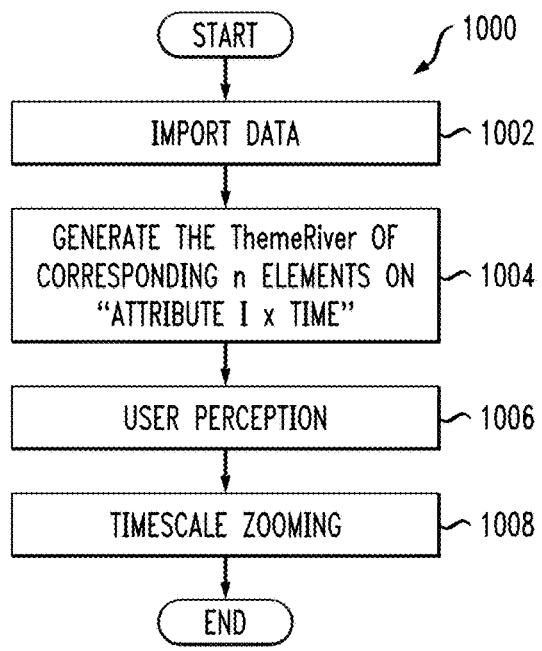
FIG. 10 shows a methodology for visual analysis using a theme river visualization in accordance with one embodiment of the invention.

FIG. 10 shows an illustrative embodiment of visual analysis methodology 1000 using a theme river (step 808).

Step 1002: The system imports the two-dimensional table BTable (Attribute I, Time).

Step 1004: The system reads the corresponding data from the BTable according to n elements which are selected by the user at step 804, and generates a theme river view of "Attribute I×Time."

Step 1006: User perception. The user analyzes the theme river view and observes the trend of how each element of Attribute I changes over time. Comparison of trends or statistical values during a specific time period of two arbitrary elements can be performed as well.

Step 1008: Timescale Zooming. By selecting the time period through a timescale-zooming bar (on a graphical user interface of the system), the user can analyze characteristics of these n elements in each time period.

Figure 11:
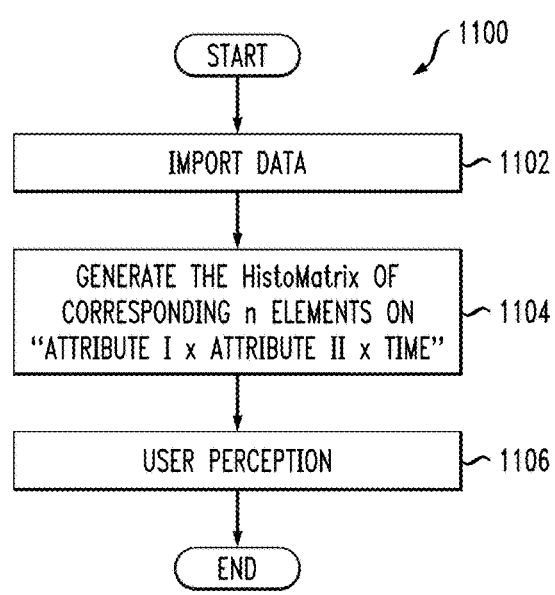
FIG. 11 shows a methodology for visual analysis using a histomatrix visualization in accordance with one embodiment of the invention.

FIG. 11 shows an illustrative embodiment of visual analysis methodology 1100 using a histomatrix (step 810).

Step 1102: The system imports the three-dimensional table TTable (Attribute I, Attribute II, Time).

Step 1104: the system reads the corresponding data from the TTable according to the n elements which are selected by the user at step 804, and generates a histomatrix view of "Attribute I×Attribute II×Time."

Step 1106: User perception. The user analyzes the histomatrix view to observe the relationship between each element of Attribute I and each element of Attribute II at different time periods.

Given the above illustrative embodiments, we now present an illustrative case study.

By taking the analysis of a mobile Internet log data as an example, in conjunction with FIG. 8 as described above, we present a use case for the progressively interactive analysis methodology of time-related cross attributes.

In this case, assume the user wants to analyze a mobile Internet log data, especially the statistics on website traffic, mobile operating systems running on mobile devices, and the relationships between them. Assume the relevant information and parameters include:

Attribute I: website traffic;
Attribute II: mobile operating system;
The elements of Attribute I are the website names;
BTable(Site, Time): traffic statistics of each website in each time period; and TTable(Site, OS, Time): traffic statistics of each website in each time period, as well as the operating systems used by mobile devices accessing the website.

We now explain how the user can use a visualization methodology according to one or more illustrative embodiments to analyze the log data.

The user selects the time period as, for example, from 2012-4-9 18:35 to 2012-4-10 01:15.

Figure 12:
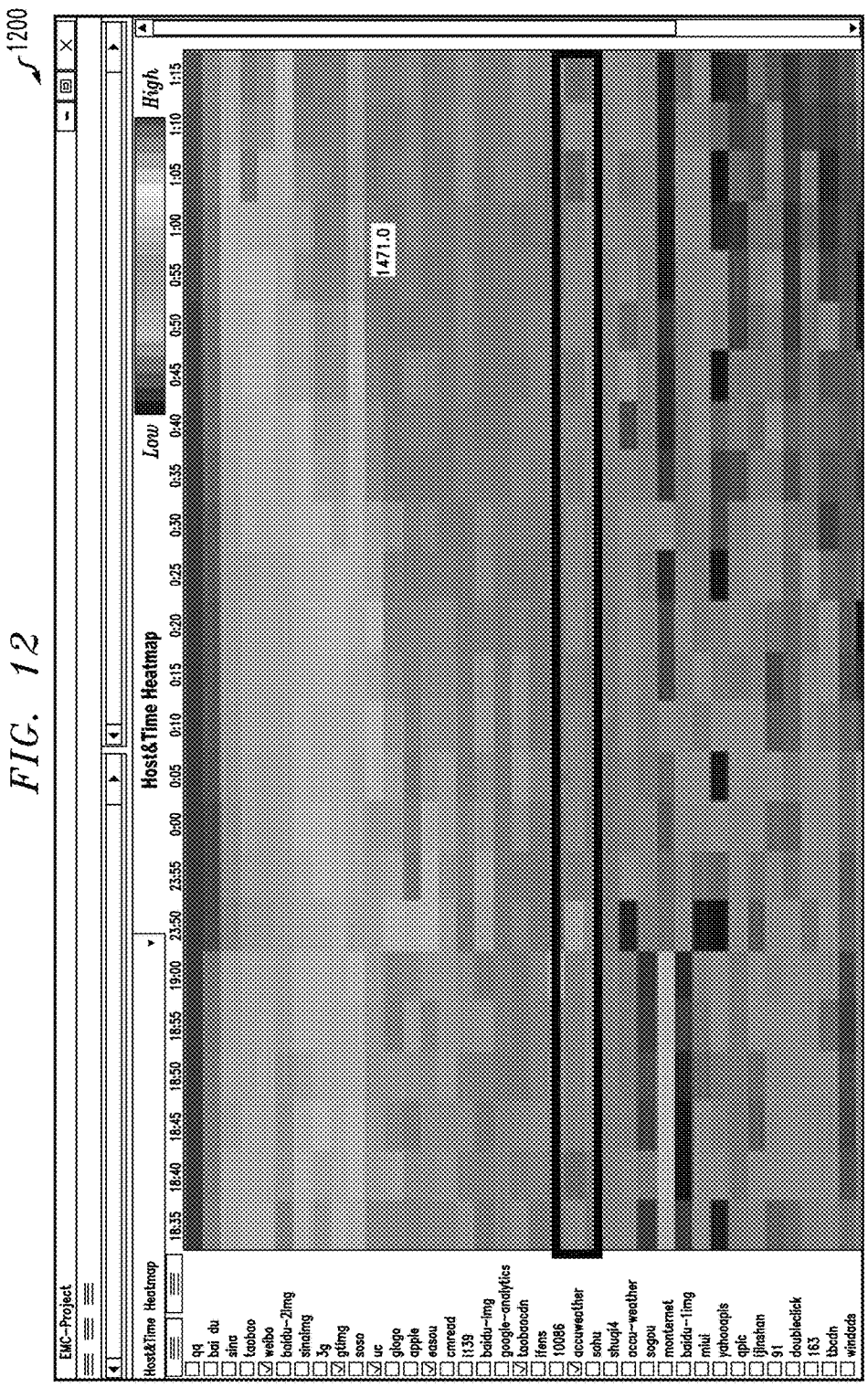
FIG. 12 shows a heat map visualization for an illustrative use case in accordance with one embodiment of the invention.

According to the two-dimensional table BTable(Site, Time), the methodology generates the heat map view 1200 within the specific time period, as shown in FIG. 12, where Y-axis represents "Websites" and X-axis represents "Time." The time interval is 5-minute time interval. Color changes from one color to another (e.g., blue at the bottom of the heat map to red at the top of the heat map, shown only as gray scale in FIG. 12) reflect the increase of websites' traffic within each time period. Thus, the user can visually analyze how the traffic of each website changes over time.

Through the heat map analysis, the user finds some patterns of interest. Compared to other websites, "accuweather" has a different varying trend of traffic, i.e., its traffic decreases over time. So assume that the user wants to conduct further analysis. Then, the user selects six websites (weibo, gtimg, uc, easou, taobaocdn and accuweather) of interest.

Figure 13:
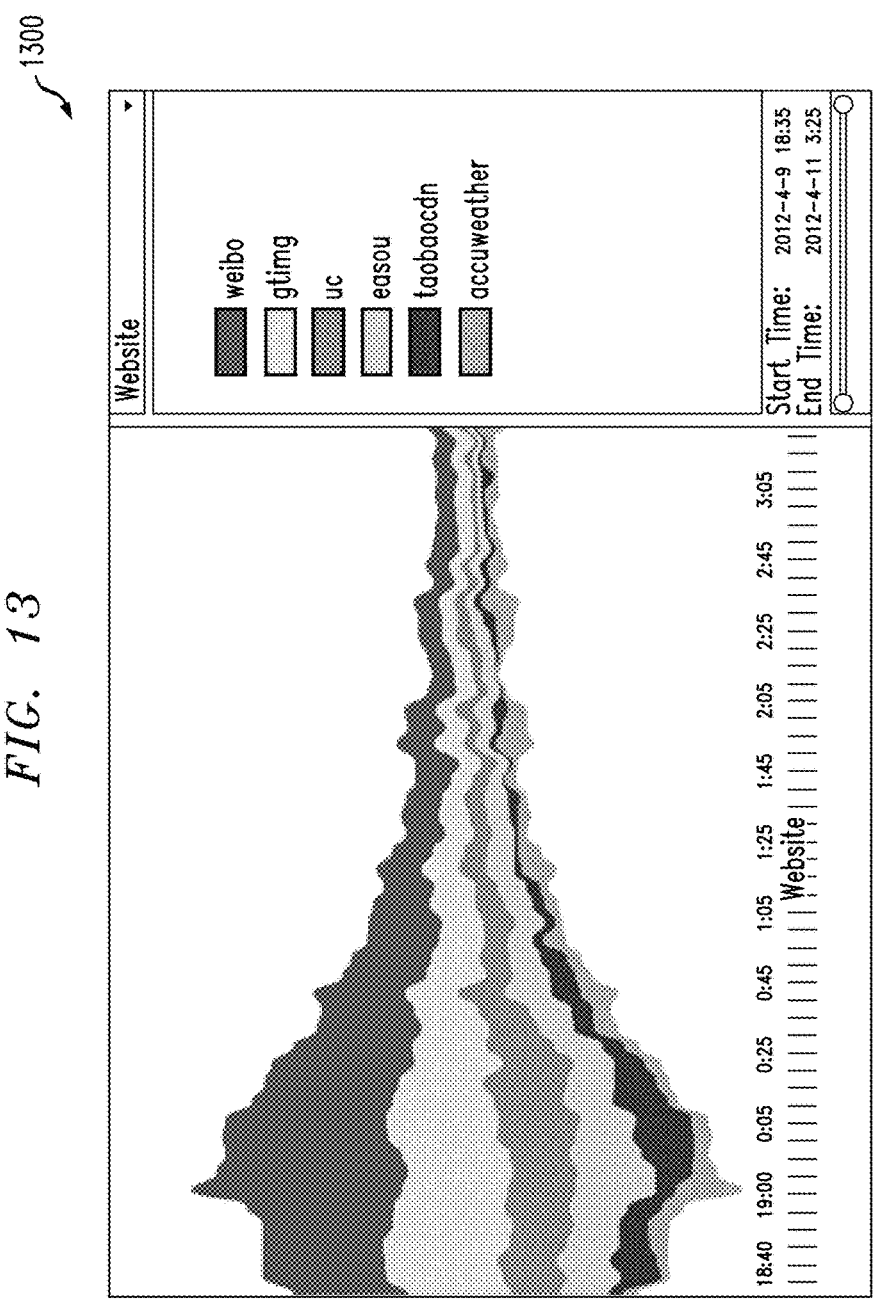
FIG. 13 shows a theme river visualization for an illustrative use case in accordance with one embodiment of the invention.

As shown in FIG. 13, a corresponding theme river view 1300 of the above six websites is generated, allowing the user to perform further analysis. Different from other ribbons which narrow down as time goes on (from left to right), the last ribbon (at bottom of river) which represents "accuweather" remains steady, and sparks periodically. Besides, the user can use the timescale-zooming function to verify the discovery by dividing time periods into finer-grained time periods.

Figure 14:
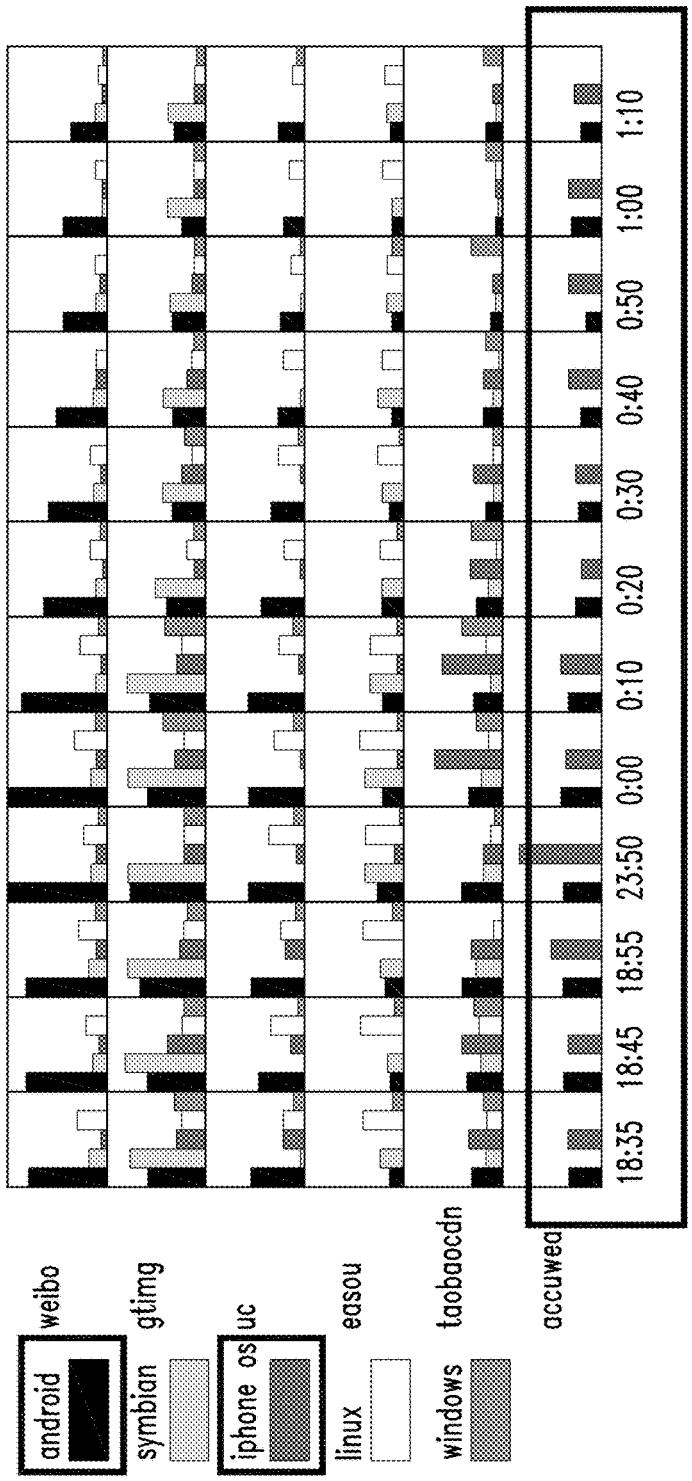
FIG. 14 shows a histomatrix visualization for an illustrative use case in accordance with one embodiment of the invention.

As shown in FIG. 14, a histomatrix view 1400 of TTable (Site, OS, Time) is generated according to the selected six websites and Attribute II (mobile operating system), and highlights the relationship among traffics of websites, operating system market shares and time. The discovery made using the theme river view 1300 can be verified in the histomatrix view 1400 with regard to the individuality of "accuweather." In addition, by analyzing cross attributes between "Site" and "OS," the user finds out that operating systems that are used to access "accuweather" are limited to "android" and "iphone os," while other websites involve all kinds of operating systems.

After the analysis of selected websites, the user can go back to the heat map and select other websites of interest. For those websites, similarly, the progressively interactive analysis of time-related cross attributes can be performed by repeating the above steps.

Figure 15:
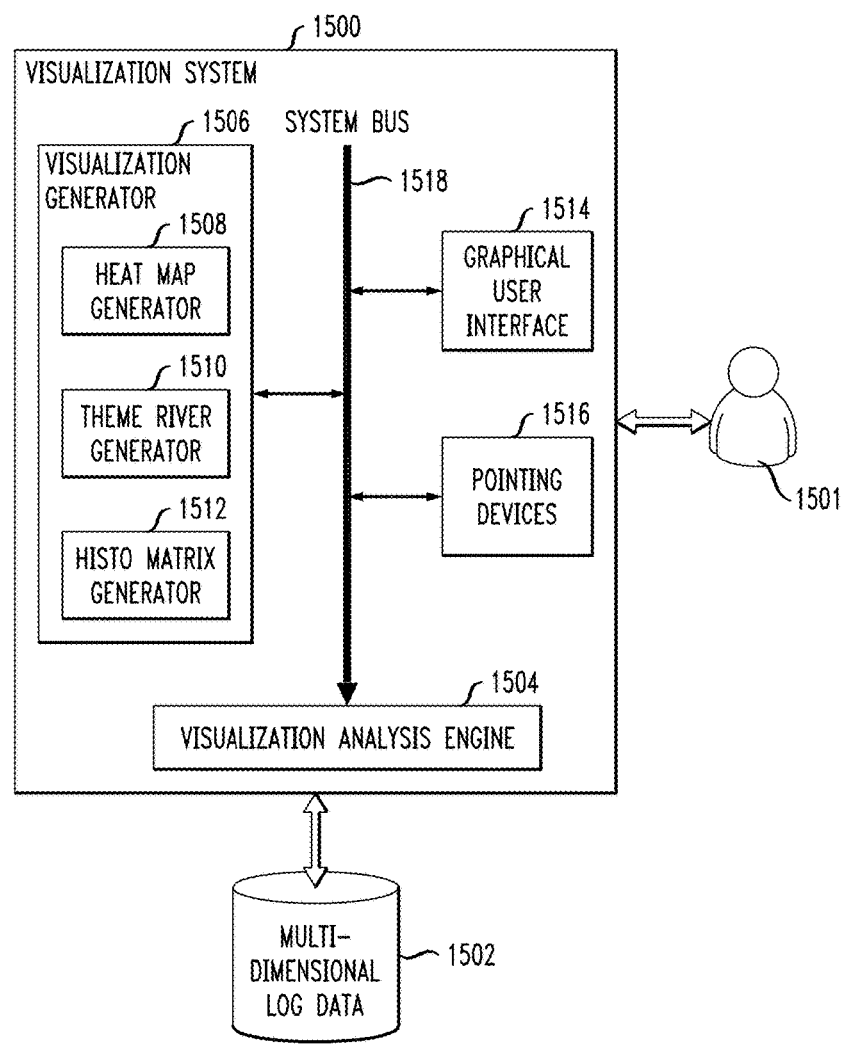
FIG. 15 shows a visualization system in accordance with one embodiment of the invention.

FIG. 15 illustrates a visualization (or visual analytics) system 1500 in which the various methodologies and visualizations of FIGS. 4-14 are implemented. As shown, the visualization system 1500 is used by a user 1501, and receives as input multi-dimensional log data 1502 (although embodiments are not intended to be limited to such a type of data). The visualization system 1500 comprises a visualization analysis engine 1504, a visualization generator 1506, which includes a heat map view generator 1508, a theme river view generator 1510 and a histomatrix view generator 1512, a graphical user interface 1514 and pointing devices 1516, all coupled via system bus 1518.

The visualization analysis engine 1504 and the visualization generator 1506 (and the various view generators 1508, 1510 and 1512) perform the computation, analysis and visualization generation steps described herein. One ordinarily skilled in the art will appreciate which component can be configured to perform which step and, in fact, the system can alternatively be configured to perform the functions described herein using a single component or more than two components. The graphical user interface 1514 and the pointing devices. 1516 enable the user 1501 to see the various views associated with the multi-dimensional log data 1502 and take actions such as, but not limited to, selecting, zooming, viewing, and visually analyzing information displayed on the graphical user interface 1514. One or more pointing devices can be implemented (e.g., mouse, trackpad, touchscreen, etc.) in the visualization system 1500.

Figure 16:
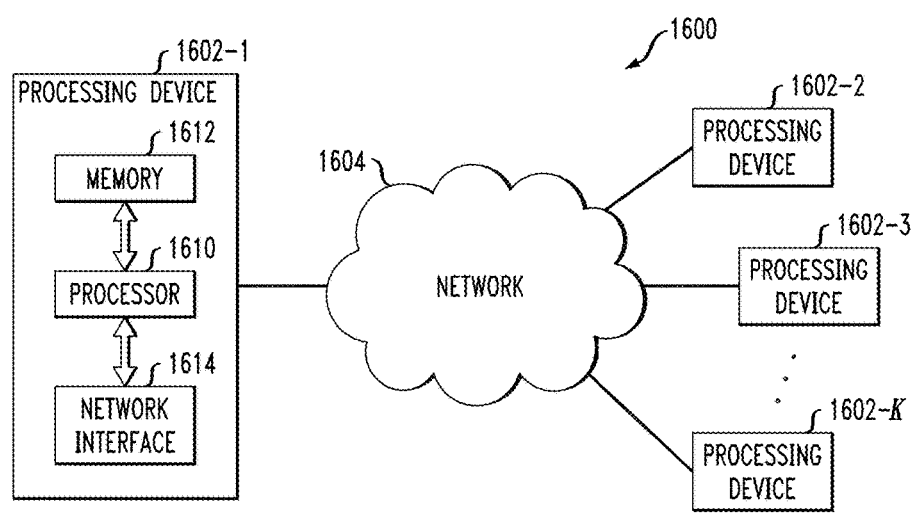
FIG. 16 shows processing infrastructure on which a visualization system and methodologies are implemented in accordance with one embodiment of the invention.

As an example of a processing platform on which a visualization system (e.g., visualization system 1600), comprising visualization functionalities as described herein, may be implemented is data processing platform 1600 shown in FIG. 16. The processing platform 1600 in this embodiment comprises a plurality of processing devices, denoted 1602-1, 1602-2, 1602-3, . . . 1602-K, which communicate with one another over a network 1604. It is to be appreciated that the visualization methodologies described herein may be executed in one such processing device 1602, or executed in a distributed manner across two or more such processing devices 1602. It is to be further appreciated that a server, a client device, a computing device or any other processing platform element may be viewed as an example of what is more generally referred to herein as a "processing device." As illustrated in FIG. 16, such a device generally comprises at least one processor and an associated memory, and implements one or more functional modules for instantiating and/or controlling features of systems and methodologies described herein. Multiple elements or modules may be implemented by a single processing device in a given embodiment.

The processing device 1602-1 in the processing platform 1600 comprises a processor 1610 coupled to a memory 1612. The processor 1610 may comprise a microprocessor, a microcontroller, an application-specific integrated circuit (ASIC), a field programmable gate array (FPGA) or other type of processing circuitry, as well as portions or combinations of such circuitry elements. Components of a computing system as disclosed herein can be implemented at least in part in the form of one or more software programs stored in memory and executed by a processor of a processing device such as processor 1610. Memory 1612 (or other storage device) having such program code embodied therein is an example of what is more generally referred to herein as a processor-readable storage medium. Articles of manufacture comprising such processor-readable storage media are considered embodiments of the invention. A given such article of manufacture may comprise, for example, a storage device such as a storage disk, a storage array or an integrated circuit containing memory. The term "article of manufacture" as used herein should be understood to exclude transitory, propagating signals.

Furthermore, memory 1612 may comprise electronic memory such as random access memory (RAM), read-only memory (ROM) or other types of memory, in any combination. The one or more software programs when executed by a processing device such as the processing device 1602-1 causes the device to perform functions associated with one or more of the components/steps of system/methodologies in FIGS. 4-15. One skilled in the art would be readily able to implement such software given the teachings provided herein. Other examples of processor-readable storage media embodying embodiments of the invention may include, for example, optical or magnetic disks.

Processing device 1602-1 also includes network interface circuitry 1614, which is used to interface the device with the network 1604 and other system components. Such circuitry may comprise conventional transceivers of a type well known in the art.

The other processing devices 1602 of the processing platform 1600 are assumed to be configured in a manner similar to that shown for computing device 1602-1 in the figure.

The processing platform 1600 shown in FIG. 16 may comprise additional known components such as batch processing systems, parallel processing systems, physical machines, virtual machines, virtual switches, storage volumes, etc. Again, the particular processing platform shown in the figure is presented by way of example only, and system 400 may include additional or alternative processing platforms, as well as numerous distinct processing platforms in any combination.

Also, numerous other arrangements of servers, clients, computers, storage devices or other components are possible in system 1600. Such components can communicate with other elements of the system 1600 over any type of network, such as a wide area network (WAN), a local area network (LAN), a satellite network, a telephone or cable network, or various portions or combinations of these and other types of networks.

Furthermore, it is to be appreciated that the processing platform 1600 of FIG. 16 can comprise virtual machines (VMs) implemented using a hypervisor. A hypervisor is an example of what is more generally referred to herein as "virtualization infrastructure." The hypervisor runs on physical infrastructure. As such, the visualization techniques illustratively described herein can be provided in accordance with one or more cloud services. The cloud services thus run on respective ones of the virtual machines under the control of the hypervisor. Processing platform 1600 may also include multiple hypervisors, each running on its own physical infrastructure. Portions of that physical infrastructure might be virtualized.

As is known, virtual machines are logical processing elements that may be instantiated on one or more physical processing elements (e.g., servers, computers, processing devices). That is, a "virtual machine" generally refers to a software implementation of a machine (i.e., a computer) that executes programs like a physical machine. Thus, different virtual machines can run different operating systems and multiple applications on the same physical computer. Virtualization is implemented by the hypervisor which is directly inserted on top of the computer hardware in order to allocate hardware resources of the physical computer dynamically and transparently. The hypervisor affords the ability for multiple operating systems to run concurrently on a single physical computer and share hardware resources with each other.

An example of a commercially available hypervisor platform that may be used to implement portions of the processing platform 1600 in one or more embodiments of the invention is the VMware vSphere® (VMware Inc. of Palo Alto, Calif.) which may have an associated virtual infrastructure management system such as the VMware vCenter®. The underlying physical infrastructure may comprise one or more distributed processing platforms that include storage products such as VNX® and Symmetrix VMAX®, both commercially available from EMC Corporation of Hopkinton, Mass. A variety of other computing and storage products may be utilized to implement the one or more cloud services that provide the visualization functionality and features described herein.

It should again be emphasized that the above-described embodiments of the invention are presented for purposes of illustration only. Many variations may be made in the particular arrangements shown. For example, although described in the context of particular system and device configurations, the techniques are applicable to a wide variety of other types of data processing systems, processing devices and distributed virtual infrastructure arrangements. In addition, any simplifying assumptions made above in the course of describing the illustrative embodiments should also be viewed as exemplary rather than as requirements or limitations of the invention. Numerous other alternative embodiments within the scope of the appended claims will be readily apparent to those skilled in the art.

What is claimed is:

1. A method comprising:
    obtaining a set of multidimensional log data, the set of multidimensional log data comprising a plurality of attributes associated with at least one website;
    parsing the set of multidimensional log data to generate a set of formatted data, the set of formatted data comprising a set of data tables;
    receiving selection of: at least one of the plurality of attributes; and one of a set of visual analysis tasks for the selected at least one attribute, the set of visual analysis tasks comprising a first visual analysis task comprising analysis of values of a given one of the attributes over time, a second visual analysis task comprising correlation analysis between two of the plurality of attributes, and a third visual analysis task comprising correlation analysis among three of the plurality of attributes;
    generating a visualization for the selected visual analysis task and the selected at least one attribute using one or more of the set of data tables in the set of formatted data;
    presenting the generated visualization on a graphical user interface; and
    enabling interactive analysis of time-related cross attributes by modifying the presentation on the graphical user interface by changing a visualization type of the generated visualization responsive to at least one of: changing the selected at least one attribute; and changing selection of one or more elements of the selected at least one attribute;
    wherein the method is performed by at least one processing device comprising a processor coupled to a memory.

2. The method of claim 1, wherein selection of the first visual analysis task further comprises selection of one of a set of visual analysis sub-tasks, the set of visual analysis sub-tasks comprising a first sub-task for analyzing an attribute value varying trend of the given attribute and a second sub-task for analyzing an attribute value distribution of the given attribute.

3. The method of claim 2, wherein:
    the first sub-task of the first visual analysis task is associated with a first visualization type;
    the second sub-task of the first visual analysis task is associated with a second visualization type;
    the second visual analysis task is associated with the second visualization type; and
    the third visual analysis task is associated with a third visualization type.

4. The method of claim 3, wherein the generated visualization comprises, for the first sub-task of the first visual analysis task, the first visualization type comprising a representation of thematic variations over time with respect to two or more elements of the given attribute.

5. The method of claim 3, wherein the generated visualization comprises, for the second sub-task of the first visual analysis task, the second visualization type comprising a heat map representation of changes in value of one or more elements of the given attribute over time using varying color.

6. The method of claim 3, wherein the generated visualization comprises, for the second visual analysis task, the second visualization type comprising a heat map representation of relationships between one or more elements of a first attribute and one or more elements of a second attribute using varying color.

7. The method of claim 3, wherein the generated visualization comprises, for the third visual analysis task, the third visualization type comprising a grid of histograms representation comprising one or more histograms representing relationships between one or more elements of a first attribute, one or more elements of a second attribute, and one or more elements of a third attribute.

8. The method of claim 7, wherein the first attribute is time, and wherein the representation comprises a grid of histograms each representing a time value and comprising bars representing values of elements of the second attribute correlated with one of the values of elements of the third attribute.

9. The method of claim 8, wherein generating the visualization comprises utilizing one or more of the two-dimensional tables responsive to selection of the first visual analysis task or the second visual analysis task.

10. The method of claim 1, wherein the set of data tables comprises one or more two-dimensional tables, each two-dimensional table representing statistics on correlation between values of elements of a first attribute and values of elements of a second attribute.

11. The method of claim 1, wherein the set of data tables comprises one or more three-dimensional tables, each three-dimensional table representing statistics on correlation between values of elements of a first attribute, values of elements of a second attribute, and values of elements of a third attribute.

12. The method of claim 11, wherein generating the visualization comprises utilizing one or more of the three-dimensional tables responsive to selection of the third visual analysis task.

13. An apparatus comprising:
    at least one processing device comprising a processor coupled to a memory;
    the at least one processing device being configured:
        to obtain a set of multidimensional log data, the set of multidimensional log data comprising a plurality of attributes associated with at least one web site;
        to parse the set of multidimensional log data to generate a set of formatted data, the set of formatted data comprising a set of data tables;
        to receive selection of: at least one of the plurality of attributes; and one of a set of visual analysis tasks for the selected at least one attribute, the set of visual analysis tasks comprising a first visual analysis task comprising analysis of values of a given one of the attributes over time, a second visual analysis task comprising correlation analysis between two of the plurality of attributes, and a third visual analysis task comprising correlation analysis among three of the plurality of attributes;
to generate a visualization for the selected visual analysis task and the selected at least one attribute using one or more of the set of data tables in the set of formatted data;
to presenting the generated visualization on a graphical user interface; and
to enable interactive analysis of time-related cross attributes by modifying the presentation on the graphical user interface by changing a visualization type of the generated visualization responsive to at least one of: changing the selected at least one attribute; and changing selection of one or more elements of the selected at least one attribute.

14. The apparatus of claim 13, wherein selection of the first visual analysis task further comprises selection of one of a set of visual analysis sub-tasks, the set of visual analysis sub-tasks comprising a first sub-task for analyzing an attribute value varying trend of the given attribute and a second sub-task for analyzing an attribute value distribution of the given attribute.

15. The apparatus of claim 14, wherein:
the first sub-task of the first visual analysis task is associated with a first visualization type;
the second sub-task of the first visual analysis task is associated with a second visualization type;
the second visual analysis task is associated with the second visualization type; and
the third visual analysis task is associated with a third visualization type.

16. The apparatus of claim 15, wherein the generated visualization comprises:
for the first sub-task of the first visual analysis task, the first visualization type comprising a representation of thematic variations over time with respect to two or more elements of the given attribute;
for the second sub-task of the first visual analysis task, the second visualization type comprising a heat map representation of changes in value of one or more elements of the given attribute over time using varying color;
for the second visual analysis task, the second visualization type comprising a heat map representation of relationships between one or more elements of a first attribute and one or more elements of a second attribute using varying color; and
for the third visual analysis task, the third visualization type comprising a grid of histograms representation comprising one or more histograms representing relationships between one or more elements of a first attribute, one or more elements of a second attribute, and one or more elements of a third attribute.

17. An article of manufacture comprising a processor-readable storage medium having encoded therein executable code of one or more software programs, wherein the one or more software programs when executed by at least one processing device cause the at least one processing device: to obtain a set of multidimensional log data, the set of multidimensional log data comprising a plurality of attributes associated with at least one website; to parse the set of multidimensional log data to generate a set of formatted data, the set of formatted data comprising a set of data tables; to receive selection of: at least one of the plurality of attributes; and one of a set of visual analysis tasks for the selected at least one attribute, the set of visual analysis tasks comprising a first visual analysis task comprising analysis of values of a given one of the attributes over time, a second visual analysis task comprising correlation analysis between two of the plurality of attributes, and a third visual analysis task comprising correlation analysis among three of the plurality of attributes; to generate a visualization for the selected visual analysis task and the selected at least one attribute using one or more of the set of data tables in the set of formatted data; to presenting the generated visualization on a graphical user interface; and to enable interactive analysis of time-related cross attributes by modifying the presentation on the graphical user interface by changing a visualization type of the generated visualization responsive to at least one of: changing the selected at least one attribute; and changing selection of one or more elements of the selected at least one attribute.

18. The article of manufacture of claim 17, wherein selection of the first visual analysis task further comprises selection of one of a set of visual analysis sub-tasks, the set of visual analysis sub-tasks comprising a first sub-task for analyzing an attribute value varying trend of the given attribute and a second sub-task for analyzing an attribute value distribution of the given attribute.

19. The article of manufacture of claim 18, wherein:
the first sub-task of the first visual analysis task is associated with a first visualization type;
the second sub-task of the first visual analysis task is associated with a second visualization type;
the second visual analysis task is associated with the second visualization type; and
the third visual analysis task is associated with a third visualization type.

20. The article of manufacture of claim 19, wherein the generated visualization comprises:
for the first sub-task of the first visual analysis task, the first visualization type comprising a representation of thematic variations over time with respect to two or more elements of the given attribute;
for the second sub-task of the first visual analysis task, the second visualization type comprising a heat map representation of changes in value of one or more elements of the given attribute over time using varying color;
for the second visual analysis task, the second visualization type comprising a heat map representation of relationships between one or more elements of a first attribute and one or more elements of a second attribute using varying color; and
for the third visual analysis task, the third visualization type comprising a grid of histograms representation comprising one or more histograms representing relationships between one or more elements of a first attribute, one or more elements of a second attribute, and one or more elements of a third attribute.

* * * * *